(12) United States Patent
von Campenhausen

(10) Patent No.: US 12,100,275 B2
(45) Date of Patent: Sep. 24, 2024

(54) DMS—INTERACTIVE PRODUCT IDENTIFICATION FOR A CALL CENTER

(71) Applicant: Roche Diabetes Care, Inc., Indianapolis, IN (US)

(72) Inventor: Harald von Campenhausen, Ladenburg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 181 days.

(21) Appl. No.: 17/843,580

(22) Filed: Jun. 17, 2022

(65) Prior Publication Data

US 2022/0327902 A1 Oct. 13, 2022

Related U.S. Application Data

(63) Continuation of application No. PCT/EP2020/087003, filed on Dec. 18, 2020.

(30) Foreign Application Priority Data

Dec. 19, 2019 (EP) ..................................... 19217805

(51) Int. Cl.
*G08B 13/196* (2006.01)
*H04N 7/18* (2006.01)
*H04N 23/661* (2023.01)

(52) U.S. Cl.
CPC . *G08B 13/19645* (2013.01); *G08B 13/19656* (2013.01); *H04N 7/181* (2013.01); *H04N 23/661* (2023.01)

(58) Field of Classification Search
CPC ............ G08B 13/196; G08B 13/19656; G08B 13/19645; H04N 7/181
See application file for complete search history.

(56) References Cited

U.S. PATENT DOCUMENTS

| | | | |
|---|---|---|---|
| 6,523,010 B2 * | 2/2003 | Lauffer | ............. G06Q 10/0631 705/7.14 |
| 9,600,982 B2 | 3/2017 | MacIntosh | |

(Continued)

FOREIGN PATENT DOCUMENTS

| | | |
|---|---|---|
| EP | 3 483 780 A1 | 5/2019 |
| RU | 2 493 599 C2 | 9/2013 |

OTHER PUBLICATIONS

International Search Report and Written Opinion of the International Searching Authority, PCT/EP2020/087003, Apr. 12, 2021, 11 pages.

(Continued)

*Primary Examiner* — Olisa Anwah

(74) *Attorney, Agent, or Firm* — Bose McKinney & Evans LLP

(57) ABSTRACT

This disclosure lies in the field of a computer implemented method of routing a video call from a call center computer system comprising a controller, a transceiver, and a machine learning system, to a product service agent computer system assigned to a certain medical device product type and associated services. This disclosure involves using artificial intelligence in order to identify a medical device product based on recorded product image data. Further aspects of this disclosure provide a corresponding call center computer system for routing a video call initiated by a mobile device from the call center computer system to a medical device product service agent computer system as well as a computer-implemented method for generating a model of a medical device product type.

10 Claims, 9 Drawing Sheets

(56) References Cited

U.S. PATENT DOCUMENTS

| | | |
|---|---|---|
| 2001/0010043 A1 | 7/2001 | Lauffer |
| 2002/0004753 A1* | 1/2002 | Perkowski ............ G06Q 30/02 |
| | | 705/26.62 |
| 2004/0081799 A1 | 4/2004 | Kaminsky et al. |
| 2010/0026817 A1 | 2/2010 | Ryan et al. |
| 2014/0052555 A1 | 2/2014 | MacIntosh |
| 2014/0098209 A1 | 4/2014 | Neff |
| 2021/0134279 A1* | 5/2021 | Mallenahally ...... G10L 15/1822 |
| 2022/0084654 A1* | 3/2022 | Flaherty ................ G16H 20/60 |

OTHER PUBLICATIONS

Anonymous, White Paper: How Computer Vision AI is Transforming Customer Care, Jan. 1, 2018, Retrieved from the Internet: URL:https://techsee.me/wp-content/uploads/2018/03/Smart-Vision_How-Computer-Vision-AI-Transforms-Customer-Service_WP_Mar18.pdf.

* cited by examiner

DMS—INTERACTIVE PRODUCT IDENTIFICATION FOR A CALL CENTER

RELATED APPLICATIONS

This application is a continuation of PCT/EP2020/087003, filed Dec. 18, 2020, which claims priority to EP 19 217 805.1, filed Dec. 19, 2019, both of which are hereby incorporated herein by reference.

BACKGROUND

This disclosure lies in the field of a computer implemented method of routing a video call from a call center computer system comprising a controller, a transceiver, and a machine learning system, to a product service agent computer system assigned to a certain medical device product type and associated services. This disclosure involves using artificial intelligence in order to identify a medical device product based on recorded product image data. Further aspects of this disclosure provide a corresponding call center computer system for routing a video call initiated by a mobile device from the call center computer system to a medical device product service agent computer system as well as a computer-implemented method for generating a model of a medical device product type.

Teleservices including telehealth and product support services have benefited from the advent of computer power, widespread availability of networks and mobile devices equipped with cameras which enable two parties engaged in a communication carried out using mobile devices such as smartphones equipped with cameras and computers to easily and conveniently exchange information between the parties encoded in audio or video signals.

In the field of medical device products, their use and services that relate to such products an important part of the communication between a user of a medical device engaged in a communication with a service provider or health care professional is to establish which specific medical device the user is referring to so as to ensure that the ensuing communication allows the product service agent including a call-center agent, a medical device product manager or a health care professional, to base his service or health consultation on the correctly identified product. If the specific medical device of the user, for example a certain model of an insulin pump, is not correctly identified by the product service agent, he may not be able to understand the technical problem associated with the relevant medical device product the user is conveying to him, let alone provide an adequate solution the user is seeking during the service call. In view of the fact that medical devices are used for the management of health and diseases, unlike other consumer devices their use is associated with a significant health risk. As a consequence, in a service call setting it is vital for the safety of medical device use and management that the medical devices are correctly identified.

The widespread use of barcodes, QR codes and text recognition and other coded product identifiers available on a product has greatly simplified the image-based identification of products in general. However, many problems in medical device product recognition persist because, e.g., a) the customer may be unable to find a product identifier on the medical device product either because it is difficult to find or because the customer may be handicapped or impaired in his ability to analyze the medical device product;

b) the product identifier may only be present on the medical device product package but not on the medical device product itself and the package may not be available anymore; and c) the product identifier appearing on the surface of the medical device product may wear off over time and not be readable anymore.

To address such issues, it has been proposed to identify products with passive tags that can be sensed by radio (e.g., RFID and NFC chips). However, the high costs of these tags are an obstacle. Other technologies have also been tried. For example, U.S. Publication No. 2004/0081799 describes how a marking can be applied to supermarket packaging by adding a polymer layer that defines scannable information in the form of matte and glossy areas. The matte/glossy areas can form indicia such as barcodes, or digital watermarks. However, this technology requires applying a polymer layer to the packaging—a further expense, and a potential health risk considering that medical device products often have to pass ambitious requirements for biocompatibility to avoid any health hazard, e.g., when the product repetitively comes into contact with the skin.

SUMMARY

Therefore there is a need to provide a system which overcomes the shortcomings associated with the prior art and which provides an inexpensive, convenient or reliable identification of a medical device product in the context of a service call between a user of the medical device product and the medical device service provider. Ideally, such solution would also save computer processing resources and time and increase efficiency of machine based medical device product recognition.

According to an aspect of this disclosure, it is provided a computer implemented method of routing a video call from a call center computer system comprising a controller, a transceiver, and a machine learning system, to a product service agent computer system, the method comprising:

a) Sending by the transceiver over a network to a user interface of a mobile device an invitation notification to initiate a medical device product video recording;

b) Recording medical device product video data received from the mobile device;

c) Repetitively sending by the transceiver over the network to the user interface of the mobile device a medical device product positioning notification to guide the user in positioning the medical device product into a camera of or connected to the mobile device;

d) Comparing by the machine learning system medical device product features extracted from the recorded medical device product video data to a plurality of predetermined medical device product type models wherein each of the models is associated with a medical device product type;

e) Ranking by the machine learning system the medical device product types associated with a predetermined medical device product type model based on their degree of identity with the compared to medical device product features extracted from the recorded medical device product video data in step d);

f) Selecting by the controller at least one candidate of the medical device product types based on the ranking in step e);

g) Sending by the transceiver over the network to the user interface of the mobile device an image for each of the selected at least one candidate of the medical device product type;

h) Receiving by the controller from a user via the user interface of the mobile device an indication which of the at least one displayed candidate of the medical device product types corresponds to the recorded medical device product; and i) Routing by the controller over the network the video call of the mobile device to a product service agent computer system assigned to the identified medical device product type.

The method of this disclosure allows a user of a medical device product seeking a service regarding the product or its use to efficiently connect in a video call to a product service agent in charge of providing a service for the specific medical device product type, while avoiding that the user needs to undergo a lengthy complicated procedure of identifying product codified medical device product identifiers such as a bar code, a serial number, etc. This disclosure also avoids that user needs to walk through a lengthy dialogue of answering many questions aimed at identifying the specific medical device product type before the call center computer system is able to route his call to the competent product service agent in charge of the medical device product type. This disclosure is also associated with a number of advantageous effects: this disclosure increases the capacity and efficiency of the call center computer system in handling service requests per time because for each service call the time needed to identify the user of a medical device product type corresponding to the user' medical device product is reduced and accordingly, the overall time of the service call can be reduced. This disclosure not only reduces the costs for service agent salaries per call but also the costs for computer hours per call and the amount of computer resources used per call. The image based medical device product identification as well as the feedback loop with the user to indicate to candidate medical device product type the user' medical device product corresponds allows for a reliable identification of the medical device product type and therefore, increases the safety of medical device product use, management and the services associated with such medical device products. An embodiment of the method of this disclosure is described in FIG. 6.

In another preferred embodiment the method further includes prior to the sending step a) a step of receiving by the transceiver a video call request by the mobile device. This step is generally carried out when the user initiates the video call over the network to the call center computer system.

In another preferred embodiment the method further includes prior to the ranking step e) a step of assigning by the machine learning system a degree of identity, e.g., an identity score, to each predetermined medical device product type model which is compared with the medical device product features extracted from the recorded medical device product video data in step d), wherein each predetermined medical device product type model is associated with a medical device product type. The calculation of such degree of identity, sometimes also referred to as confidence score is generally known to the skilled worker and is, for example, described in U.S. Pat. No. 9,600,982B2 and EP3483780A1 which is hereby incorporated by reference.

In the context of this disclosure, the meaning of the terms "routing of a video call" is generally known to the skilled artisan and preferably refers to the process of selecting a path for traffic in a network or between or across multiple networks to connect a mobile device with a call center computer system or with a part thereof such as the transceiver or with another computer system such as the product service agent computer system or a part thereof. It also covers the process, preferably controlled by the call center computer system or a part thereof, of switching the video call connection between the mobile device and the call center computer system or a part thereof to a connection between the between the mobile device and the product service agent computer system or a part thereof. Generally, the routing process redirects the connection from the mobile device over the network with the call center computer system to a connection with the product service agent computer system based on a routing tables which associate the address of a given product service agent computer system with that product service agent computer system's assigned role to conduct video calls for certain predefined medical device product types. The routing tables maintain a record of the routes to various network destinations. Routing tables may be specified by an administrator, learned by observing network traffic or built with the assistance of routing protocols. The routing can be performed in many types of networks, including circuit-switched networks, such as the public switched telephone network (PSTN), and computer networks, such as the Internet as well as in wired or wirelessly connected networks which directly or indirectly connect a mobile device with a call center computer system or a part thereof or with a product agent computer system or a part thereof. In the context of this disclosure, the routing table may store information of medical device product service agent computer system addresses and the medical device product type(s) which the medical device product service agent computer systems having certain addresses are responsible for. This way, when the medical device product type associated with the user's medical device product is identified the controller of the call center computer system is able to identify and route the call to the adequate medical device product service agent computer system in charge of such identified medical device product type based on the corresponding routing address of the product service agent computer system stored in the routing table. The routing table, may be stored in the medical device product type database.

In the context of this disclosure, the meaning of the terms "call center" is generally known to the skilled artisan and preferably refers to a group of persons or agents, including medical device product service agents, of a business or organization who serve users such as patients, caretakers of patients, customers, health care professionals such as nurses and doctors. The call centers preferably communicate with the user over the user's mobile device.

In the context of this disclosure, the meaning of the terms "medical device product service agent" refers to a person who provides services to users such as patients, caretakers of patients, customers, health care professionals such as nurses and doctor. The medical device product service agent may be a technical or scientific expert, a business expert, or a health care professional such as a doctor, nurse or coach. The services are centered around the medical device product and include a) product care services such as consultation about proper product use, product settings, technical aspects, product repair, product information; b) health services for disease management, medical device data analysis, user coaching; and c) any other service associated with the medical device product and users of such products.

In the context of this disclosure, the meaning of the terms "mobile device" is generally known to the skilled artisan and preferably refers to any device which comprises a processor, a display, a camera comprised by the device or connected thereto, a user interface such as a touch screen or keys or buttons, and which device is adapted for video calls, for display of information on the mobile device user interface and for exchanging signals and data with a computer system over a network such as over a wired or wireless connection including over the Internet, a phone network, and a server connection. Preferred mobile devices are smartphones, laptops, tablets and personal computers.

In the context of this disclosure, the meaning of the terms "call center computer system" of this disclosure is generally known to the skilled artisan and preferably refers to a computer system which can be used by a call center as they are generally known in the art. The call center computer system of this disclosure comprises at least a controller, a machine learning system, and a transceiver for communicating with other devices including a mobile device and a product service agent computer system over a network. The call center computer system preferably further comprises at least one of the following, more preferably all of the following: a predetermined medical device product type model database, a computer user interface, a medical device product type database, and a medical device product type image database. The call center computer system of this disclosure may operate in the capacity of a server or a client machine in a client-server network environment, or as a peer machine in a peer-to-peer (or distributed) network environment. The computing device may be a personal computer (PC), a server, a network router. Further, while call center computer system may only comprise a single computing device the term "call center computer system" shall also be taken to include any collection of machines (e.g., computers) that individually or jointly execute a set (or multiple sets) of instructions to perform any one or more of the methodologies discussed herein.

In the context of this disclosure, the meaning of the term "controller" is generally known to the skilled artisan and preferably refers to a computer processor an expansion card, or a stand-alone device that interfaces with a more peripheral device, and may include one or more central processing units (CPUs), graphical processing units (GPUs), or any other processor known in the art. The controller may be a plug-in board, or a single integrated circuit on the motherboard. More generally, a controller as described herein is a device for executing machine-readable instructions stored on a computer readable medium, for performing tasks and the controller may comprise any one or combination of, hardware and firmware. A controller may also comprise memory storing machine-readable instructions executable for performing tasks. In an embodiment the controller acts upon information by manipulating, analyzing, modifying, converting or transmitting information for use by an executable procedure or an information device, and/or by routing the information to an output device over a network such as to a medical device product service agent computer system or to a mobile device.

In the context of this disclosure, the meaning of the terms "invitation notification to initiate a medical device product video recording" refers to any format of a message that invites, requests of prompts the user of a medical device engaged in a video call to start a video recording of his medical device product. The notification can be a text message or a graphical icon, image, animation, video or any other graphical element which can be displayed on the user interface of the mobile device. Initiation of the video recording may include activating the camera recording function, holding or presenting the medical device product into the camera view, adjusting the position of the mobile device or of the camera so as to put the medical device product into the camera view, displaying on the user interface of the mobile device or on another display connected to the mobile device the recorded medical device product.

In the context of this disclosure, the meaning of the terms "recording medical device product video data received from the mobile device" means that the medical device product video data captured by camera of or connected to the mobile device is sent over the network to the call center computer system. The data is received by the transceiver, forwarded to the controller and processed together with the machine learning system. The received medical device product video data may also be stored in a memory or database.

In the context of this disclosure, the meaning of the terms "machine learning system" is generally known to the skilled artisan and preferably refers to a system configured to generate a medical device product type model for each medical device product type that the machine learning system is intended to analyze in the context of this disclosure. The generation of the medical device product type models is described in detail further below. The medical device product type models may preferably be stored in the predetermined medical device product type model database. The machine learning system uses machine learning methods which can be a supervised learning method, a convolutional neural network, an unsupervised learning method, a reinforcement learning method, and is preferably a supervised learning method. Information may be pushed manually to the machine learning system for example to enrich the predetermined medical device product type model database. The machine learning methods may generate the predetermined medical device product type model based on features in obtained images of a medical device product of confirmed medical device product type identity such as shape, edge, contour, size, size proportion, angle of edges, texture, color, hue, contrast of medical device product parts of different color, and pattern of the medical device product or a part thereof. The machine learning system may also employ a pre-trained multi-layer neural network which uses a plurality of layers to extract said features of the medical device product contained in the recorded video data. The above machine learning systems are generally known to the skilled artisan and can be readily applied to this disclosure. Further information on the generation of the predetermined medical device product type model is provide below. The machine learning system and the predetermined medical device product type model database are operably connected to each other and are each also operably connected to the controller.

During the product feature extraction from the recorded medical device product video data the machine learnings system may determine that the current vantage point of the camera vis-à-vis the medical device product is unsuitable to generate medical device product video data for product recognition or that additional video data recorded from another aspect or view of the medical device product should be recorded to enrich the data set for the purpose of feature extraction; and following said determination that the vantage point is unsuitable for product recognition, the call center computer system may instruct the user to move the camera to a different vantage point or to move the presented medical device product, respectively to a different position. As the mobile device captures and sends the captured medical device product video data to the call center computer system, the latter via the transceiver repetitively sends over the network to the user interface of the mobile device a medical device product positioning notification to guide the user in positioning the medical device product into a camera of or connected to the mobile device. Methods of product feature extraction from recorded product video data using machine learning systems are generally known in the art and can be readily carried out by the skilled artisan and adapted to this disclosure.

In the context of this disclosure, the meaning of the terms "medical device product positioning notification" refers to any format of a message that invites, requests of prompts the user of a medical device engaged in a video call to continue holding or presenting the medical device product into the camera view, to keeping or adjusting the position of the mobile device or of the camera so as to change the presentation of the medical device product into the camera view, or to adjusting the position of the camera or of the medical device product as specified in that message. Such position adjustment may invite the user to tilting or turning the product, to changing the distance between the medical device product and the camera, to changing the orientation or presentation angle of the medical device product, to presenting the medical device product into the camera with removed or dressed covers, under changed light conditions, with an altered background, etc. The notification can be a text message or a graphical icon, image, animation, video or any other graphical element which can be displayed on the user interface of the mobile device.

By way of the displayed medical device product positioning notification the call center computer system can help the user to easily understand how to present the medical device product into the view of the camera so as to ensure that the call center computer system quickly receives additional image data necessary to enable the machine learning system to carry out medical device product feature extraction from the recorded image data, to compare the extracted medical device product features with the plurality of predetermined medical device product type models and to rank the medical device product types associated with a predetermined medical device product type model based on their degree of identity with the compared to medical device product features. Accordingly, medical device product identification can be carried out reliably, quickly, efficiently and convenient-to-the-user. This way, this disclosure allows for a reliable identification of the medical device product type and therefore, increases the safety of medical device product use, management and the services associated with such medical device products.

In an embodiment of this disclosure, the product features are extracted by the machine learning system from the recorded medical device product video data by methods generally known to the skilled person in the art which can be readily carried out by the skilled artisan and adapted to this disclosure. The extracted features from the video recorded data of the medical device product include at least one of shape, edge, contour, size, size proportion, angle of edges, texture, color, hue, contrast of medical device product parts of different color, and pattern of the medical device product or a part thereof.

The medical device product features extracted from the recorded medical device product video data are compared by the machine learning system to a plurality of predetermined medical device product type models wherein each of the models is associated with a medical device product type. The plurality of predetermined medical device product type models are preferably stored in the predetermined medical device product type model database and the medical device product types are, in turn, preferably stored in the medical device product type database. In a preferred embodiment of this disclosure, based on the conducted comparison step the machine learning system assigns to each compared to medical device product type model a degree of identity, preferably an identity score, indicating to what extent the processed extracted set of medical device product features from the recorded video data is identical to or matches the medical device product type associated with the scored medical device product type model. In one embodiment, the medical device product identity score is higher the more the more medical device product features extracted from the recorded medical device product video data are identical with the corresponding features of the medical device product type model and vice versa.

The terms "predetermined medical device product type model" preferably refers to a model generated for a medical device product type by the machine learning system using the methods described herein including the computer-implemented method for generating a model of a medical device product type described herein below. The models are referred to as predetermined because they are generated before they are used in the machine learning system based feature extraction, comparison and ranking steps of the subject matter of this disclosure described herein. In a preferred embodiment terms "predetermined medical device product type model" refer to a model generated for a medical device product type using at least 2 of, preferably a plurality of images obtained of a specimen of the medical device product type selected from any of set a) and/or b) in combination with any of set c) and/or d) below:

Set a) images from a certified product database comprising images from medical device product specimen of proven medical device product type identity;

Set b) images downloaded from the internet or from a commercially available database, which images were categorized by a technical expert to represent a medical device product type;

Set c) images taken from a given medical device product specimen with a confirmed identify different from the medical device product type to be trained on;

Set d) images that were downloaded by an image crawler searching the internet or from a commercially available databases and stored in an image database. In one embodiment, the downloaded images were searched based on the name of the medical device product type or based on an image based web search that identifies images using an uploaded image of a product specimen of a certain medical device product type. The downloaded images are subsequently checked and selected by a technical expert to ensure that only images depicting a given medical device product specimen different from a given medical device product type to be trained on are included.

These images and their uses are described in more detail below.

The terms of this disclosure, "a medical device product type is associated with a predetermined medical device product type model" means that each medical device product type stored in the medical device product type database is represented by a corresponding predetermined medical device product type model which is stored in the predetermined medical device product type model database.

Following the comparison step the machine learning system preferably ranks the medical device product types associated with a predetermined medical device product type model based on the degree of identity, e.g., the identity score, with the compared to medical device product features extracted from the recorded medical device product video data. To this end, the medical device product types associated with the assessed predetermined medical device product type models may be ordered in decreasing order from those having the highest assigned degree of identity to the lowest degree of identity. The ranking may be stored in conjunction with the video call identity in a memory accessible to the controller.

The controller selects the at least one candidate of the medical device product types based on the ranking. Preferably at least 2, at least 3, at least 4, at least 5, at least 6 or at least 7 candidate of the medical device product types are selected. For each selected candidate of the medical device product type an image is send by the transceiver over the network to the user interface of the mobile device, preferably for display on the user interface of the mobile device.

The displayed images of the candidates of the medical device product type can then be assessed by the user to support or confirm the medical device product type identification by the call center computer system.

The controller may receive from a user via the user interface of the mobile device over the network an indication which of the at least one displayed candidate of the medical device product types corresponds to the recorded medical device product. This indication can be provided in any format, by voice or text message, by touching the presented candidate images on the touch screen user interface, by selecting a number displayed in conjunction with an image representing the candidate image, etc.

The controller will route over the network the video call of the mobile device to a product service agent computer system assigned to the identified medical device product type which is operated by a product service agent who is specialized and trained to provide a service to the user that is tailored to the specific medical device product identified in the method of this disclosure.

In another embodiment the controller does not receive from the user an indication which of the at least one displayed candidate of the medical device product types corresponds to the recorded medical device product or the user notifies the call center computer system that he is not able to identify the medical device product type. According to one embodiment the call center computer system will then send more information for each candidate medical device product type previously sent to the user interface to facility the medical device product type identification by the user, wherein the information may comprise a medical device product type specific feature notification for each candidate medical device product type previously sent to the mobile device. In an alternative embodiment, the call center computer updates the set of at least one image of candidate medical device product type previously sent with at least one image of another candidate medical device product type from the next rank in order.

In another preferred embodiment of the method of this disclosure, steps b) and c) are repeated until the recording of the medical device product video data has been completed. As the medical device product features are extracted from the recorded medical device product video data and analyzed by the machine learning system it also checks if the available data is sufficient to enable the comparison of extracted data with the predetermined medical device product type models and the ranking of medical device product types associated with a predetermined medical device product type model based on their degree of identity with the compared to medical device product features extracted from the recorded medical device product video data. In one embodiment, the recording of the medical device product video data has been completed when at least one of the following conditions is met:

The recorded medical device product video data comprises least the front view of the medical device product;

The recorded medical device product video data comprises a recording of all sides of the medical device product; and The recorded medical device product video data comprises at least 50%, at least 60%, at least 70%, at least 80%, at least 90% of the product features defining the predetermined medical device product type models.

Once sufficient recorded medical device product video data has been gathered the transceiver of the call center computer may send by over the network to the user interface of the mobile device a video recording status notification to indicate that the medical device product video recording has been completed. The video recording status notification can be a text message or a graphical icon, image, animation, video or any other graphical element which can be displayed on the user interface of the mobile device. The video recording status notification may inform the user of the mobile device that the medical device product video recording can be stopped.

In another preferred embodiment of the method of this disclosure, the method the image for at least one identified candidate medical device product type is displayed with at least one medical device product type specific feature notification.

In the context of this disclosure, the meaning of the terms "medical device product type specific feature" refers to a visible feature of a given medical device product type which when taken alone or in combination with other visible features allow identification of a given medical device product type and which visible feature or feature set is preferably absent from medical device products of another medical device product type. The medical device product type specific features or set of features associated with a given medical device product type are preferably stored in the medical device product type database and/or in the medical device product type image database.

In the context of this disclosure, the meaning of the terms "medical device product type specific feature notification" refers to a graphical icon, image, animation, video or any other graphical element which can be displayed with the image for at least one identified candidate medical device product type on the user interface of the mobile device. In one embodiment, the medical device product type specific feature notification and the image for at least one identified candidate medical device product type are combined to form a new image file or data signal which is then sent for display to the user interface. Alternatively, the image for at least one identified candidate medical device product type and the medical device product type specific feature notification are sent as separate files or data signals and jointly presented on the user interface. Preferably, the medical device product type specific feature notification marks-up a medical device product type specific feature in an image of that medical device product type in a way to allow the user to easily recognize which visible feature(s) of the at least one identified candidate medical device product type is a medical device product type specific feature. Examples are shown in FIGS. 5 and 9.

The display of the product type specific feature notification increases the accuracy of correct identification of the medical device product type over hitherto known methods and therefore increases the safety of medical device product use, management and the services associated with such medical device products. It also increases the efficiency and decreases the time needed to identify the product and the time needed until the video call can be routed to the appropriate medical device product service agent computer system operated by a medical device product service agent competent to provide services for the respective identified medical device product type.

In another embodiment of this disclosure, at least one further image for a candidate of the medical device product type is sent by the transceiver over the network to the user interface of the mobile device in the event that the controller does not receive from a user via the user interface of the mobile device an indication which of the at least one displayed candidate of the medical device product types corresponds to the recorded medical device product and wherein steps h) and i) are repeated.

As described above, during the ranking step the medical device product types associated with the assessed predetermined medical device product type models may be ordered in decreasing order from the those having the highest assigned degree of identity to the lowest degree of identity and the controller then selects the at least one candidate of the medical device product types based on the ranking (from top to bottom of the ranking) which is then sent for display to the user interface of the mobile device. Now, when at least one further image for a candidate of the medical device product type is sent, that one further image for a candidate of the medical device product type is selected from the position(s) in rank next to the lowest position of the initially selected at least one candidate of the medical device product types. For example, if in the selection step images of three candidates of the medical device product types with positions 1 to 3 of the ranking were selected, two further images for a candidate of the medical device product type are then chosen from the next two positions in rank after position 3, i.e., from medical device product types assigned to positions 4 and 5 in the ranking.

According to another embodiment of this disclosure, in the event the controller does not receive from a user via the user interface of the mobile device an indication which of the at least one displayed candidate and/or at least one additional candidate of the medical device product types corresponds to the recorded medical device product the call is routed by the controller to a predetermined product agent computer system. The product agent may seek identification of the medical device product type based on inspection of the recorded video data and/or by questioning the user about the recorded medical device product.

In another embodiment of this disclosure, the medical device product type is a medical device product version, generation, or release, a product associated with a specific name or trademark, selected from a class of a medical device product including a drug delivery device such as a pump or a pen, a device for medical testing such as an in vivo or in vitro body analyte meter, a physiological parameter measuring device such as a blood pressure or pulse metering device, a surgical instrument, and a wheelchair. Typically, such medical device product version, generation, or release, product associated with a specific name or trademark is manufactured by a defined manufacturer, preferably legal manufacturer, which usually can be identified in the product labeling information. Examples of such different medical device product types of the same medical device class are, e.g., in the class of Roche strip based in vitro blood glucose measuring systems the Accu-Check Aviva, the Accu-Check Aviva Nano, the Accu-Check Aviva Expert and the Accu-Check Aviva Insight products representing different medical device product types of markedly different characteristic design (see FIG. 8).

In another embodiment of this disclosure, the extracted medical device product features include at least on of shape, edge, contour, size, size proportion, angle of edges, texture, color, hue, contrast, mean, variance, gradients, filter responses, color features, geometric features, contrast of medical device product parts of different color, and patterns of the medical device product or a part thereof.

In another embodiment of this disclosure, the machine learning system may also include codified medical device product features including a logo, a trademark, text, a bar code, a serial number, and a pattern code.

In another embodiment of this disclosure, prior to step a) the transceiver sends to the to a user interface of a mobile device a predetermined menu of classes of medical device products for display on the user interface of the mobile device. The controller then receives from the mobile device an indication by the mobile device which class of medical device product the user's medical device product belongs to. By preselecting a class of medical device products the ensuing medical device product identification by the machine learning system can be carried out quicker and consumes less resources when compared to a method which omits the class selection step because the machine learning system will during the ensuing comparing step d) only compare the recorded medical device product video data only to predetermined medical device product type models belonging to the preselected class of medical device products and not include in the comparison medical device product type models belonging to different medical device product classes.

According to another aspect of this disclosure, it is provided a call center computer system as described herein adapted to carry out the methods for routing a video call from the call center computer system to a medical device product service agent computer system of this disclosure described above and below.

According to another aspect of this disclosure, it is provided a call center computer system for routing a video call from the call center computer system to a medical device product service agent computer system, the call center computer system comprising:
  a transceiver adapted to sending over a network to a user interface of a mobile device an invitation notification to initiate a medical device product video recording;
  a controller adapted to recording medical device product video data received from the mobile device;
  the transceiver being further adapted to repetitively sending over the network to the user interface of the mobile device a medical device product positioning notification to guide the user in positioning the medical device product into a camera of or connected to the mobile device;
  a machine learning system adapted to
    i. comparing device product features extracted from the recorded medical device product video data to a plurality of predetermined medical device product type models wherein each of the models is associated with a medical device product type, and
    ii. Ranking the medical device product types associated with a predetermined medical device product type model based on their degree of identity with the compared to medical device product features extracted from the recorded medical device product video data;

the controller being further adapted to selecting at least one candidate of the medical device product types based on the ranking;

the transceiver being further adapted to sending over the network to the user interface of the mobile device an image for each of the selected at least one candidate of the medical device product type;

the controller being further adapted
  i. to receive from the user via the user interface of the mobile device an indication which of the at least one displayed candidate of the medical device product types corresponds to the recorded medical device product; and
  ii. to routing over the network the video call of the mobile device to a call-center agent computer system assigned to the identified medical device product type.

In another embodiment of this disclosure, the call center computer system further comprises:

a medical device product type image database for storing images representing a medical device product type;

a predetermined medical device product type model database for storing a plurality of medical device product type models each model being associated with a medical device product type.

In yet another aspect of this disclosure, it is provided a computer-implemented method for generating a model of a medical device product type, the method comprising:
  a) receiving an identity of a medical device product type;
  b) obtaining at least two images of a specimen of the medical device product type;
  c) generating, using a machine learning system, the model of the medical device product type based on the obtained images; and
  d) storing the model in a predetermined medical device product type model database.

The stores model is preferably referred to as "predetermined medical device product type model."

This method is preferably repeated for each medical device product type listed in the list of medical device product types so as to generate model of a medical device product type for each predetermined medical device product type model stored in the model of a medical device product type model database.

In one embodiment of this disclosure, the recorded image data used to generate a final predetermined medical device product type model of this disclosure generally comes from multiple datasets. In particular, different data sets may be used in different stages of the creation of the model: a training dataset, a validation dataset and optionally also a test dataset. The use of such datasets in the generation of models and the fitting of models used in machine learning based image recognition is generally known in the art and can be readily adapted by the skilled person based on the available knowledge and the guidance provided herein. In one embodiment the images used to generate the medical device product type models can be stored in the medical device product type image database. An embodiment of the method of this disclosure is described in FIG. 7.

In one embodiment of this disclosure, to generate a predetermined medical device product type model, the model may be initially created using a "training dataset," i.e., a set of example images used to fit the parameters, e.g., weights of connections between neurons in artificial neural networks of the model. The model may then be trained on the training dataset using, e.g., a supervised learning method. In practice, the training dataset may consist of pairs of an input vector (or scalar) and the corresponding output vector (or scalar), which is commonly denoted as the target (or label). The current model may be run with the training dataset and produces a result, which may then compared to the target, for each input vector in the training dataset. Based on the result of the comparison and the specific learning algorithm being used, the parameters of the predetermined medical device product type model can be adjusted. The model fitting can include both variable selection and parameter estimation.

Successively, in one embodiment of this disclosure, the fitted predetermined medical device product type model is generally used to predict the responses for the observations in a second dataset called the "validation dataset." Preferably, the specific images forming the validation dataset should not be part of the training data set and vice versa. This way, the validation dataset may provide an unbiased evaluation of a model fit on the training dataset while tuning the model's hyperparameters. In an embodiment, the validation datasets are used for regularization by early stopping: stop training when the error on the validation dataset increases, as this is a sign of overfitting to the training dataset.

Finally, in one embodiment of this disclosure, it is used a "test dataset" which is a dataset used to provide an unbiased evaluation of a final model fit on the training dataset.

In one embodiment of this disclosure, a high quality of the generated predetermined medical device product type model associated with a given predetermined medical device product type is achieved if the machine learning system is trained with medical device product specimen depicting images of the medical device product of confirmed identity of the given predetermined medical device product type. To this end the obtained images may be chosen from at least one of the following sources:

images taken from a certified product database comprising images from medical device product specimen of proven medical device product type identity, images that were downloaded by an image crawler searching the internet or from a commercially available databases, which images that were checked and selected by a technical expert to ensure that only images depicting a medical device product specimen of a given medical device product type are included. In one embodiment, the downloaded images were searched based on the name of the medical device product type or based on an image based web search that identifies images using an uploaded image of a product specimen of a certain medical device product type.

The above-defined obtained images are referred to as "obtained images with confirmed medical device product type identity" and are preferably part of the training dataset. By the same token, a subset of images from the "obtained images with confirmed medical device product type identity" can also be used as part of the validation dataset and of the test dataset. The specific images forming each of the validation dataset, the training dataset and the test dataset should only be contained in one of the sets.

To further increase the robustness of medical device product type recognition based on the generated predetermined medical device product type model, machine learning algorithm may be trained with two sets of images:

Images of set a) comprising, preferably consisting of, obtained images with confirmed medical device product type identity, and Images of set b) comprising, preferably consisting of, obtained images with a medical device product type identity different from the medical device product type to be trained on.

The images of set b), i.e., images obtained with a medical device product type identity different from the medical device product type to be trained on may be chosen from at least one of the following sources:

images taken from a given medical device product specimen with a confirmed identify different from the medical device product type to be trained on, images that were downloaded by an image crawler searching the internet or from a commercially available databases and stored in an image database. In one embodiment, the downloaded images were searched based on the name of the medical device product type or based on an image based web search that identifies images using an uploaded image of a product specimen of a certain medical device product type. The downloaded images are subsequently checked and selected by a technical expert to ensure that only images depicting a given medical device product specimen different from a given medical device product type to be trained on are included.

Preferably such images include images from specimen of a medical device product types that look similar to the medical device product type to be trained on. The above images are preferably part of the training dataset. By the same token, a subset of these images can also be used as part of the validation dataset or of the test dataset. The specific images forming each of the validation dataset, the training dataset and the test dataset should only be contained in one of the sets.

Moreover, it is preferred that the above defined obtained images comprise 2D images including but not limited to images taken from product specimen from different camera angles, from different parts of the product specimen, from different magnification factors, from different sides of the product specimen, from product specimen of different traces of wear, from product specimen with different abrasions, from product specimen under different light and under different light reflection conditions, images taken in front of different backgrounds, and images taken with different models of cameras or mobile devices.

Preferably, the training of the machine learning system to generate a predetermined medical device product type model is repeated for each medical device product type and the resulting predetermined medical device product type model is preferably stored in the medical device product type model database and the corresponding medical device product type is stored in the medical device product type database.

The trained machine learning system which uses a given generated predetermined medical device product type model when confronted with a validation dataset or test dataset of images of set a) will output a high degree of identity, e.g., a high identity score, to indicate that these images match the trained certain medical device product type corresponding to the given generated predetermined medical device product type model. Preferably, the machine learning system using the same predetermined medical device product type model will when confronted with images of set b) will output a low degree of identity, e.g., a low identity score, to indicate that these images do not match the trained certain medical device product type corresponding to the given generated predetermined medical device product type model. The generated predetermined medical device product type models for each of the medical device product types can then be used by the machine learning system in this disclosure.

Preferably, the predetermined model of a given medical device product type is further associated with at least one medical device product type image of the given medical device product type. Such at least one image may be used for sending it to the user interface of the mobile device, e.g., when requesting an indication if the displayed candidate medical device product type corresponds to the recorded medical device product.

In another embodiment of the above computer-implemented method, the at least two obtained images of a specimen of the medical device product type are selected from:

images from a certified product database comprising images from medical device product specimen of proven medical device product type identity; and images downloaded from the internet or from a commercially available database, which images were categorized by a technical expert to represent a medical device product type.

In another embodiment of the above computer-implemented method, the obtained images comprise at images selected from 2D images, a 3D images, images taken from a specimen of the medical device product type from different camera angles, from different parts of the product specimen, from different magnification factors, from different sides of the product specimen, from specimen of different traces of wear, from specimen with different abrasions, from specimen under different light and under different light reflection conditions, images taken with different models of mobile devices and images taken with different cameras.

In a further aspect, a system for generating a predetermined model of a given medical device product type is provided which comprises a controller configured to perform the steps of the method described above, a non-transitory computer readable medium having computer-executable instructions to cause a computer system to perform the steps of the method as described above, and a computer program product comprising instructions which, when the program is executed by a computer, cause the computer to carry out the steps of the method as described above. The system for generating a predetermined model of a given medical device product type further comprises a control unit, a web portal, an image crawler, a medical device product database, a plurality of image databases, a machine learning system, and a model database.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 9 depicts examples of different medical device product types displayed with medical device product type specific feature notifications such as arrows, circles and stars.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
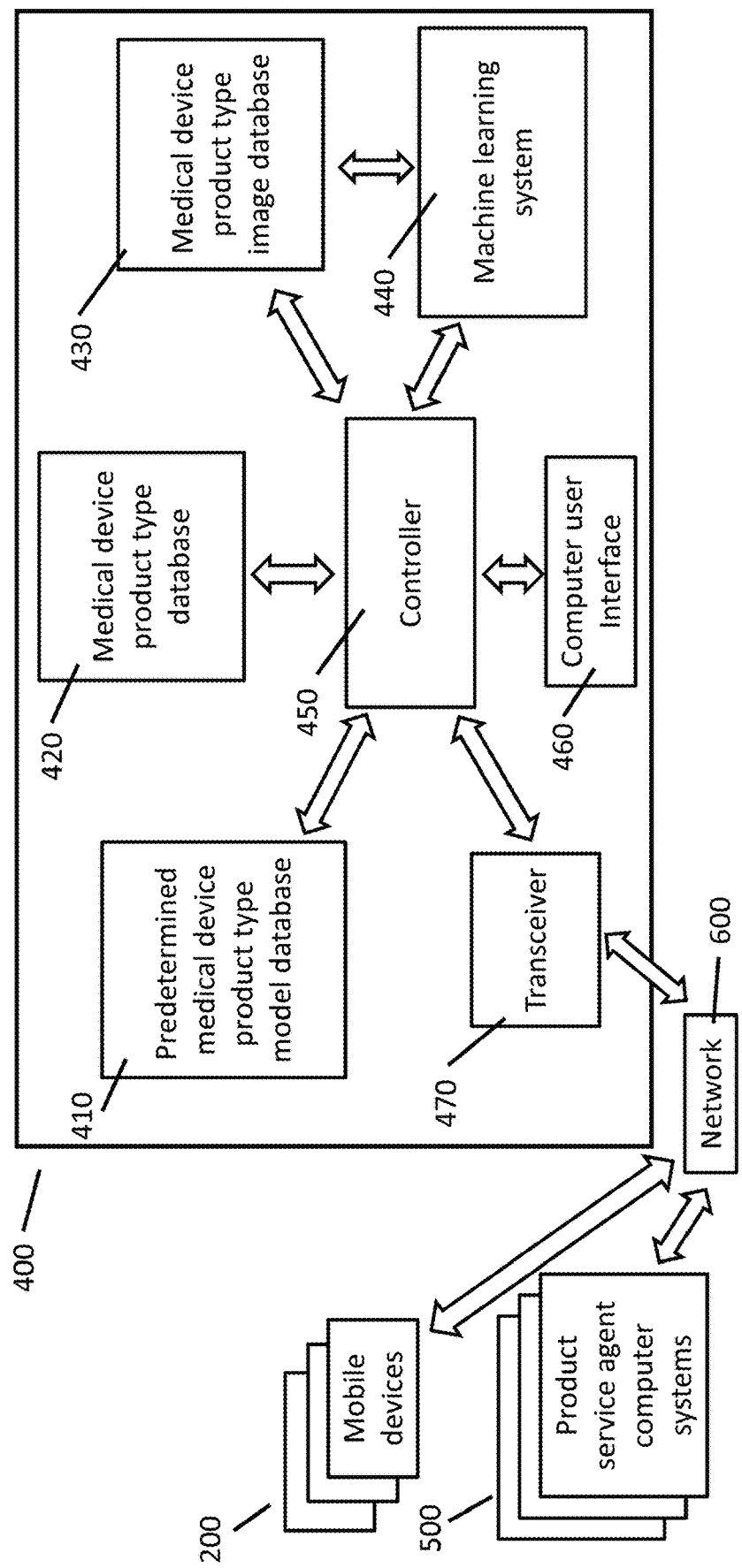
FIG. 1 depicts a block diagram of an embodiment of a call center computer system of this disclosure and connected hardware.

In the following, reference is first made to FIG. 1 which shows an embodiment of a call center computer system (400) of this disclosure having a controller (450) operably connected to a predetermined medical device product type model database (410) storing the predetermined medical device product type models, a medical device product type database (420) storing information about device product types, a medical device product type image database (430) storing images representing medical device product types, a machine learning system (440) operably connected to a medical device product type image database (430), a transceiver (470) operably connected to a controller (450), and a computer user interface (460) operably connected to a controller (450) allowing user interaction with the call center computer system. The call center computer system (400) communicates with other components of a network (600) such as product service agent computer systems (500) and mobile devices (200) via the transceiver (470).

Figure 7:
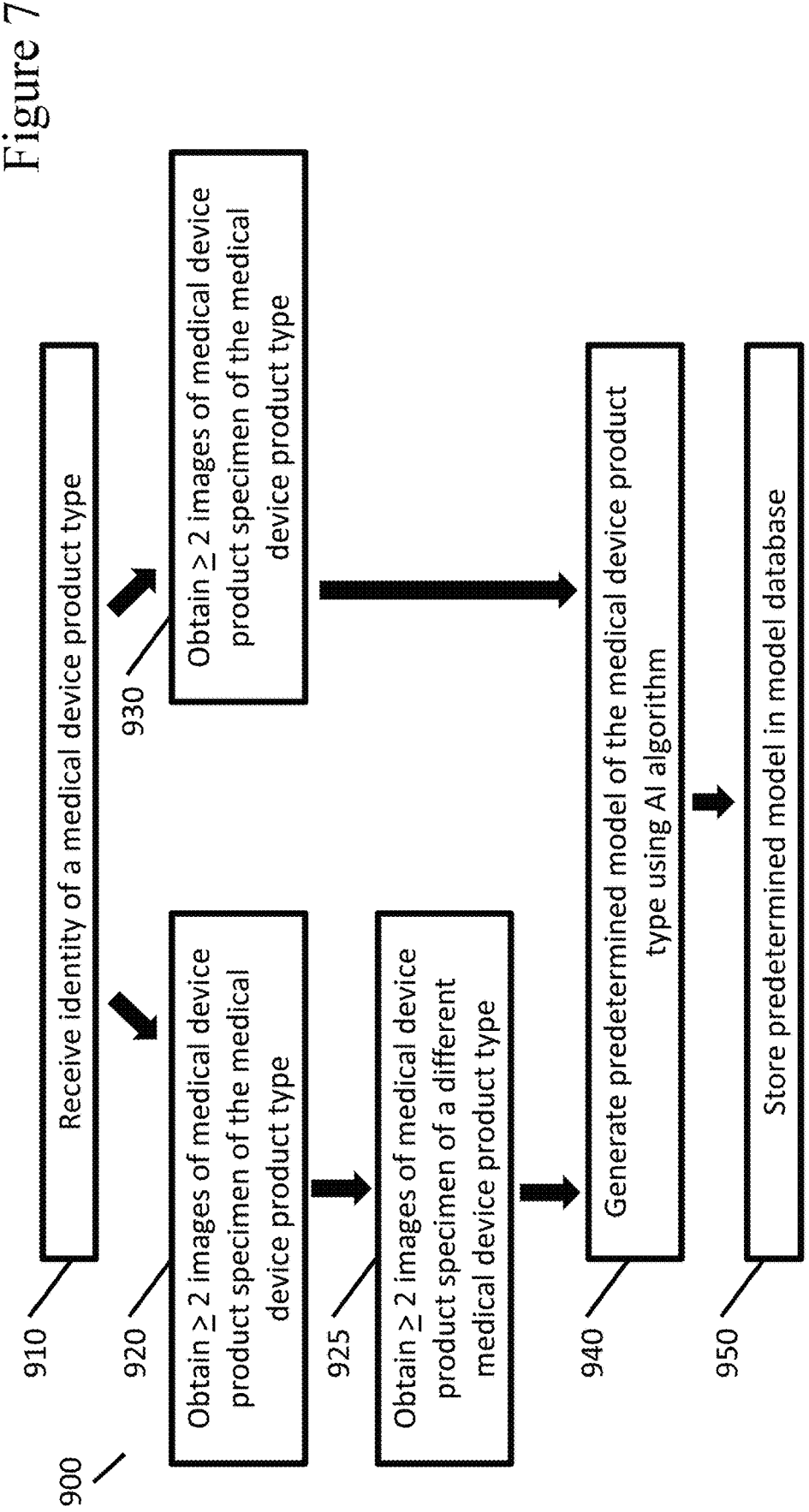
FIG. 7 depicts a flow diagram of an embodiment of this disclosure.

The medical device product type database (420) stores information about medical device product types including information that the machine learning system (440) is able to process or recognize. For example, that medical device product type database (420) may for each medical device product type store the product names, brand names, versions, etc. used for that medical device product type and optionally also medical device product service agent computer systems assigned to a given medical device product types and their respective medical device product service agent computer system routing addresses. Examples of four such medical device product type names are depicted in FIG. 7. The medical device product type database (420) may additionally store medical device product type specific feature data or product type specific feature images which can be used to send to the mobile device an image for at least one identified candidate medical device product type which is displayed with at least one medical device product type specific feature notification device product type specific feature notification.

Medical device image data received and recorded by the controller (450) over the network (600) from the mobile device (200) is assessed by the controller (440) which uses the machine learning system (440) to extract medical device product features from the recorded image data and compares the data with the predetermined medical device product type models stored in the predetermined medical device product type model database (410). Based on the conducted comparison step the machine learning system assigns to each compared-to medical device product type model a degree of identity, preferably an identity score, indicating to what extent the processed extracted set of medical device product features from the recorded video data is identical to or matches the medical device product type associated with the scored medical device product type model.

Figure 8:
FIG. 8 depicts examples of different medical device product types.

If, for example, the during the video call the user presents a specimen of an Accu-Check Aviva medical device product (see FIG. 8, 1100) into the camera of the medical device (210) and further assuming that the call center computer system (400) stored in its predetermined medical device product type model database (410) a medical device product type model for each of the product types depicted in FIG. 8, the machine learning system (440) based comparison of the recorded Accu-Check Aviva specimen image data with the respective medical device product type models for each of medical device product types Accu-Check Aviva (1100), Accu-Check Aviva Expert (1200), Accu-Check Aviva Nano (1300) and Accu-Check Aviva Insight (1400), respectively may calculate the following degrees of identity score in descending order of ranking: Accu-Check Aviva=0.98; Accu-Check Aviva Nano=0.8, Accu-Check Aviva Expert=0.68 and Accu-Check Aviva Insight=0.55. The controller (450) may then select the three medical device product types associated with the highest identity score as candidates and send respective images representing each of the selected three candidates of medical device product types via the transceiver (470) over the network (600) for display on the user interface (display (220)) of the mobile device (200) of the user (100). To facilitate product identification the images of the candidates may be displayed along with a medical device product type specific feature notifications (270) as shown in FIG. 9.

Once the user identifies his Accu-Check Aviva (1100) medical device product based on the displayed image representing the Accu-Check Aviva image, upon receiving a corresponding indication of identity from the user by the controller, the video call is routed to the predetermined product service agent computer system (500) and the predetermined service agent (700) in charge of the identified Accu-Check Aviva product type can engage in the service call with the user of the mobile device and of the Accu-Check Aviva product without having to spend time on a cumbersome identification of the relevant medical device product type used by the user.

Figure 2:
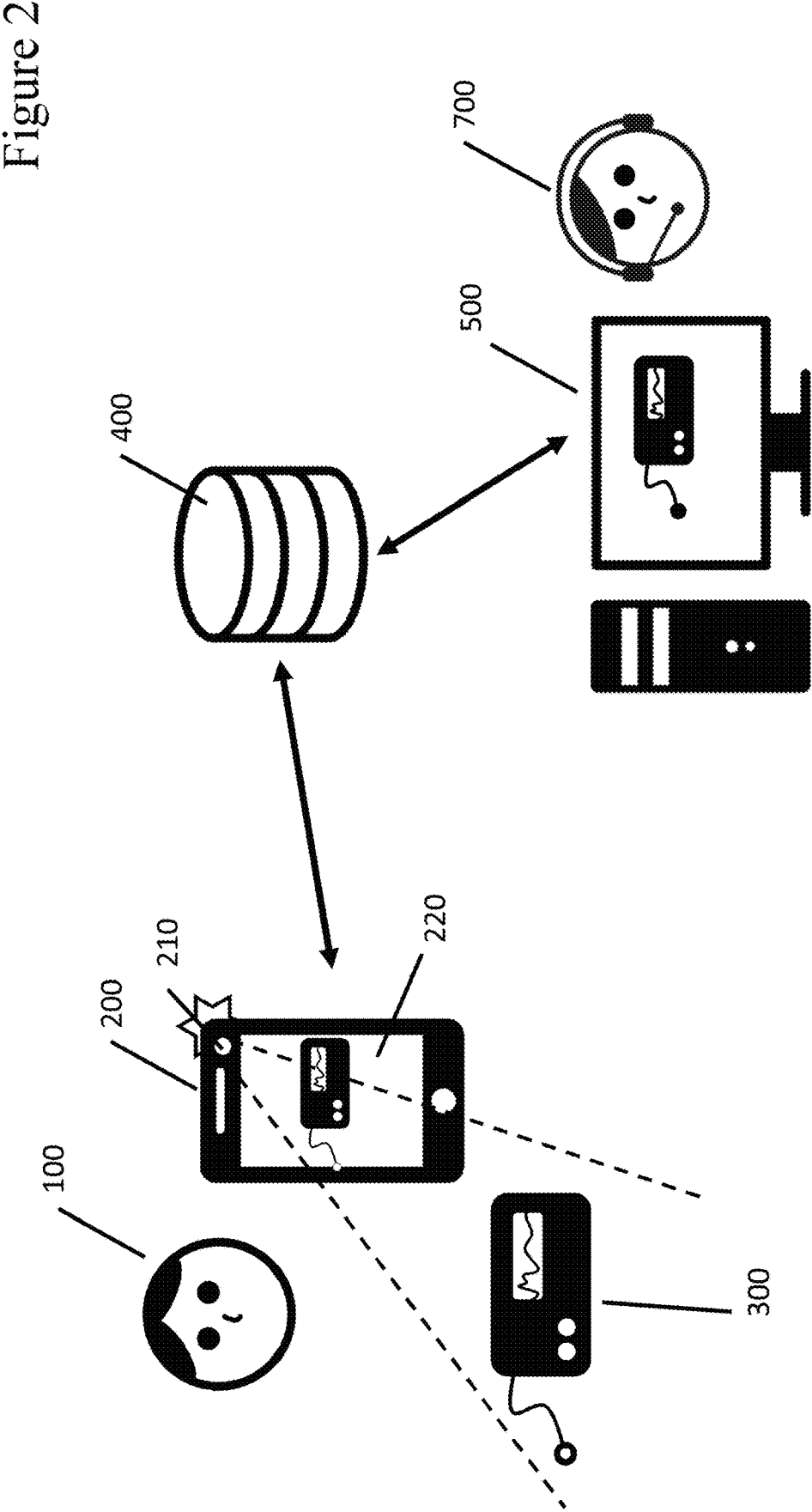
FIG. 2 depicts a diagram of an embodiment of this disclosure showing a mobile device engaged in a video call over a network with a call center computer system and a product service agent computer system connected to the call center computer system.

In the following, reference is first made to FIG. 2 which shows a user (100) who using his mobile device (200) equipped with a camera (210) recording image data of his medical device product (300) and sending the medical device product video data over a network (600) to the call center computer system (400). Once the medical device product type (300) corresponding to the recorded medical device product video data of is identified using the recorded video data and the machine learning system (440) the call center computer system (400) routes the video call to a predetermined product service agent computer system (500) operated by a product service agent (700) in charge of the identified medical device product type.

Figure 3:
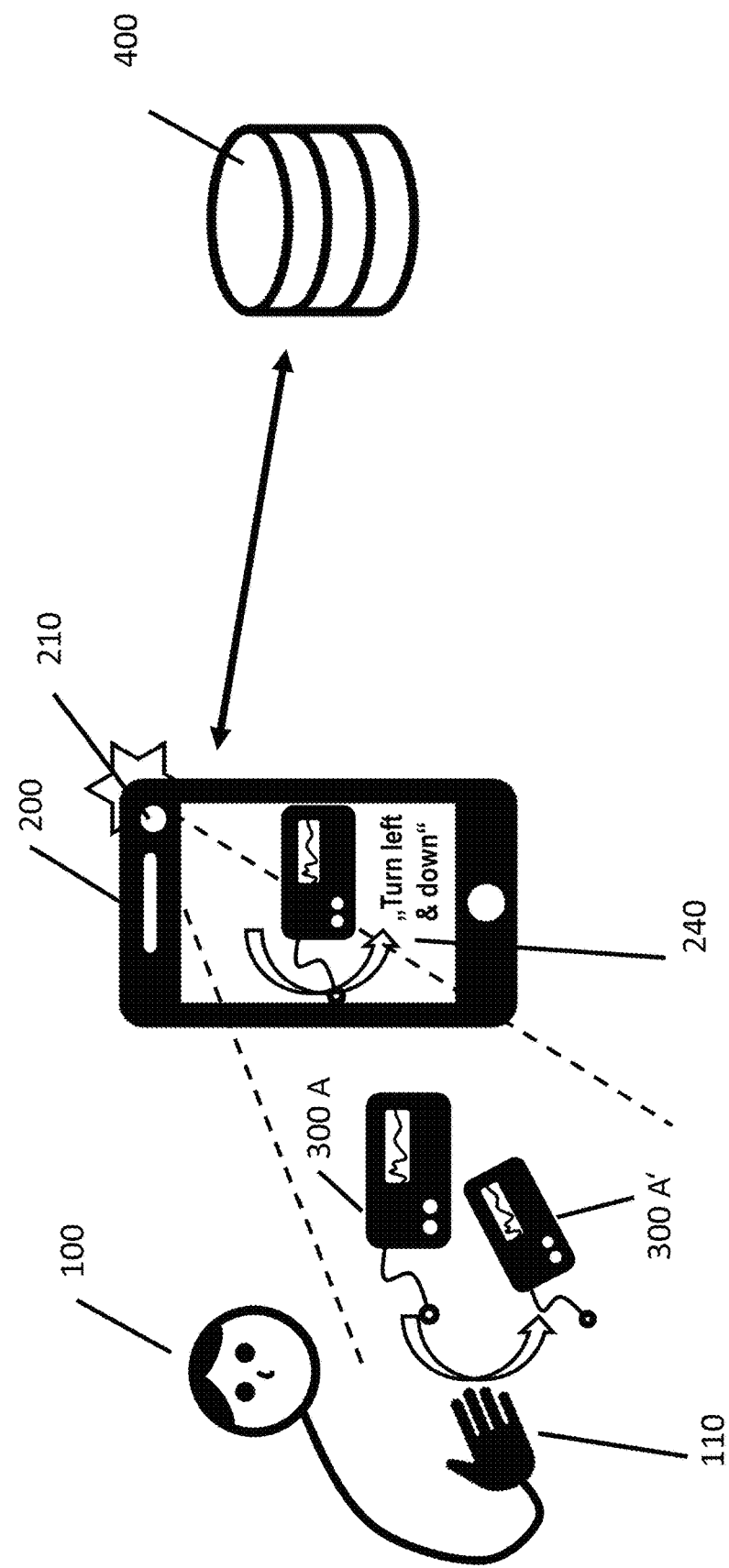
FIG. 3 depicts a diagram of an embodiment of this disclosure showing a call center computer system sending over the network to the user interface of the mobile device a medical device product positioning notification to guide the user in positioning the medical device product into a camera of or connected to the mobile device.

In the following, reference is first made to FIG. 3 which shows a user (100) who using his mobile device (200) equipped with a camera (210) recording image data of his medical device product (300) and sending the video data over a network (600) to the call center computer system (400). The mobile device product's (200) user interface displays a medical device product positioning notification (240) in the format of an arrow and a text message ("turn left & down") to guide the user in changing the video recording positioning of the medical device product from position A (300A) to position B (300B) using his hand (110) to position the medical device product (300). The medical device product positioning notification (240) is sent to the mobile device (200) by the call center computer system (400).

Figure 4:
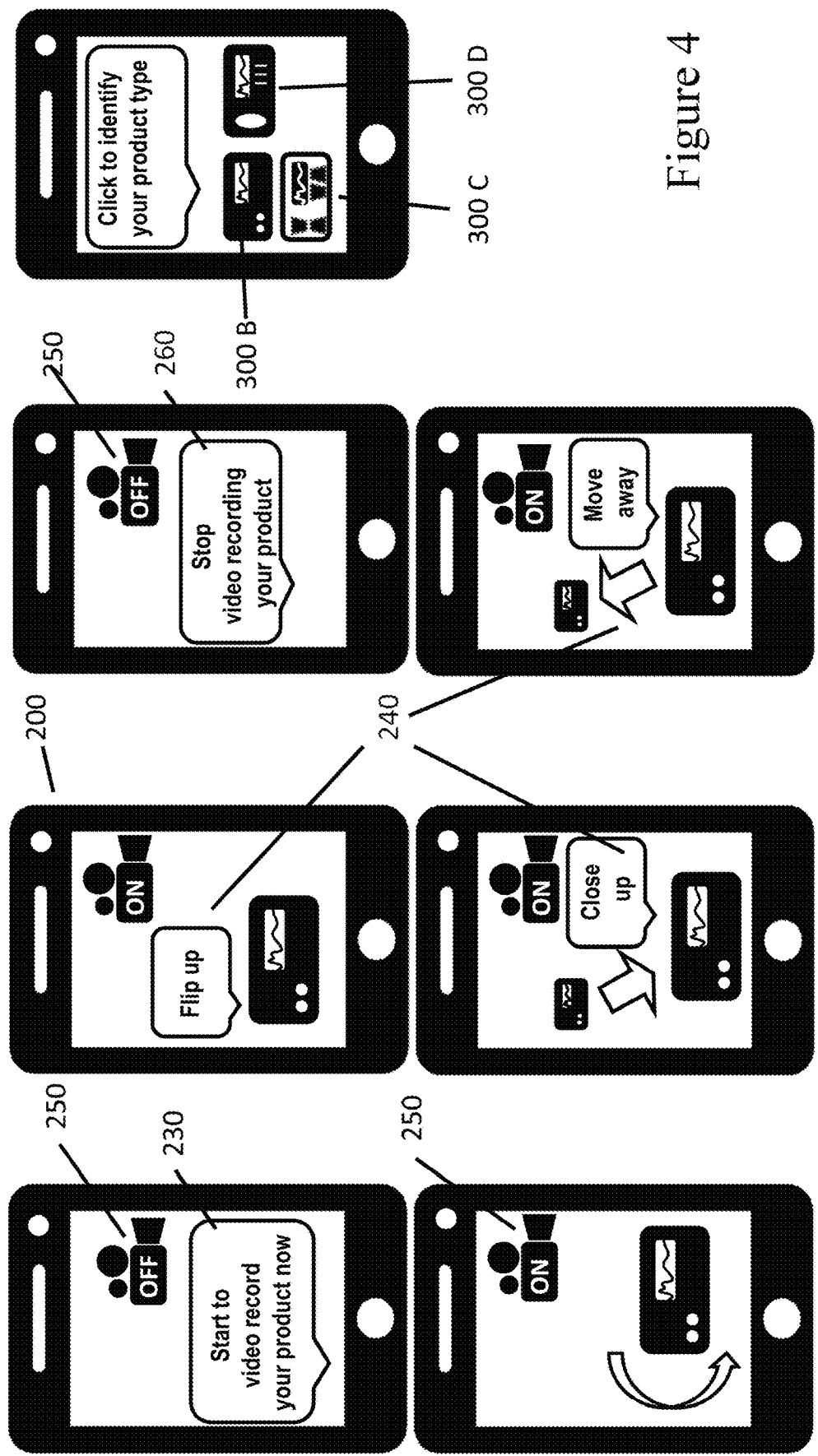
FIG. 4 depicts a diagram of an embodiment of this disclosure showing examples of user interfaces of a mobile device displaying an invitation notification, product positioning notifications, video recording status notifications and displayed candidates of the medical device product types.

In the following, reference is first made to FIG. 4 which shows examples of user interfaces of a mobile device (200) depicting examples of a) an invitation notification to initiate a medical device product video recording (230) in the form or a text message "Start to video record your product now"; b) medical device product positioning notifications (240) in the form of test messages or symbols inviting the user to flip up the presented medical device product, or to close up or move away the presented medical device product vis-à-vis the camera; c) a video recording status notification (250) shown in an icon depicting a video camera and an "on" or "off" text message indicating the status of the video recording; d) a notification to stop a medical device product video recording (260) depicted by the text "Stop video recording your product" e) candidate medical device product types B (300B), C (300C) and D (300D).

Figure 5:
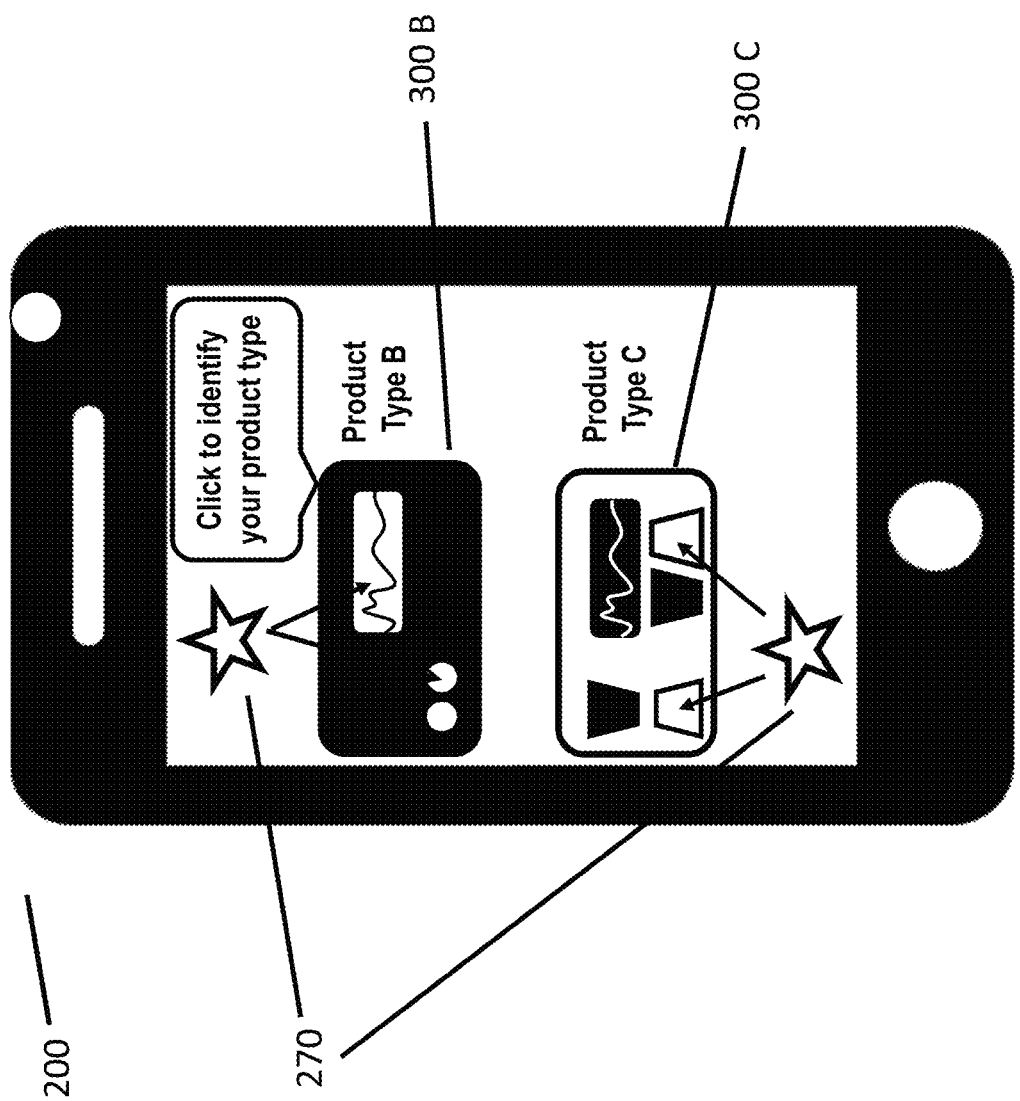
FIG. 5 depicts a diagram of an embodiment of this disclosure showing a user interface of a mobile device displaying candidate medical device product types with medical device product type specific feature notifications.

In the following, reference is first made to FIG. 5 which shows a user interface of a mobile device (200) depicting examples of candidate medical device product types B (300B) and C (300C) along with a medical device product type specific feature notifications (270) in the form of arrows or stars marking-up product type specific features to facilitate medical device product type identification by the user. For example, by clicking on the area of the touch screen displaying the respective candidate medical device product type B (300B) or C (300C) the user can send an indication to the call center computer to confirm the identity of his medical device product with one of the displayed candidate medical device product types.

Figure 6:
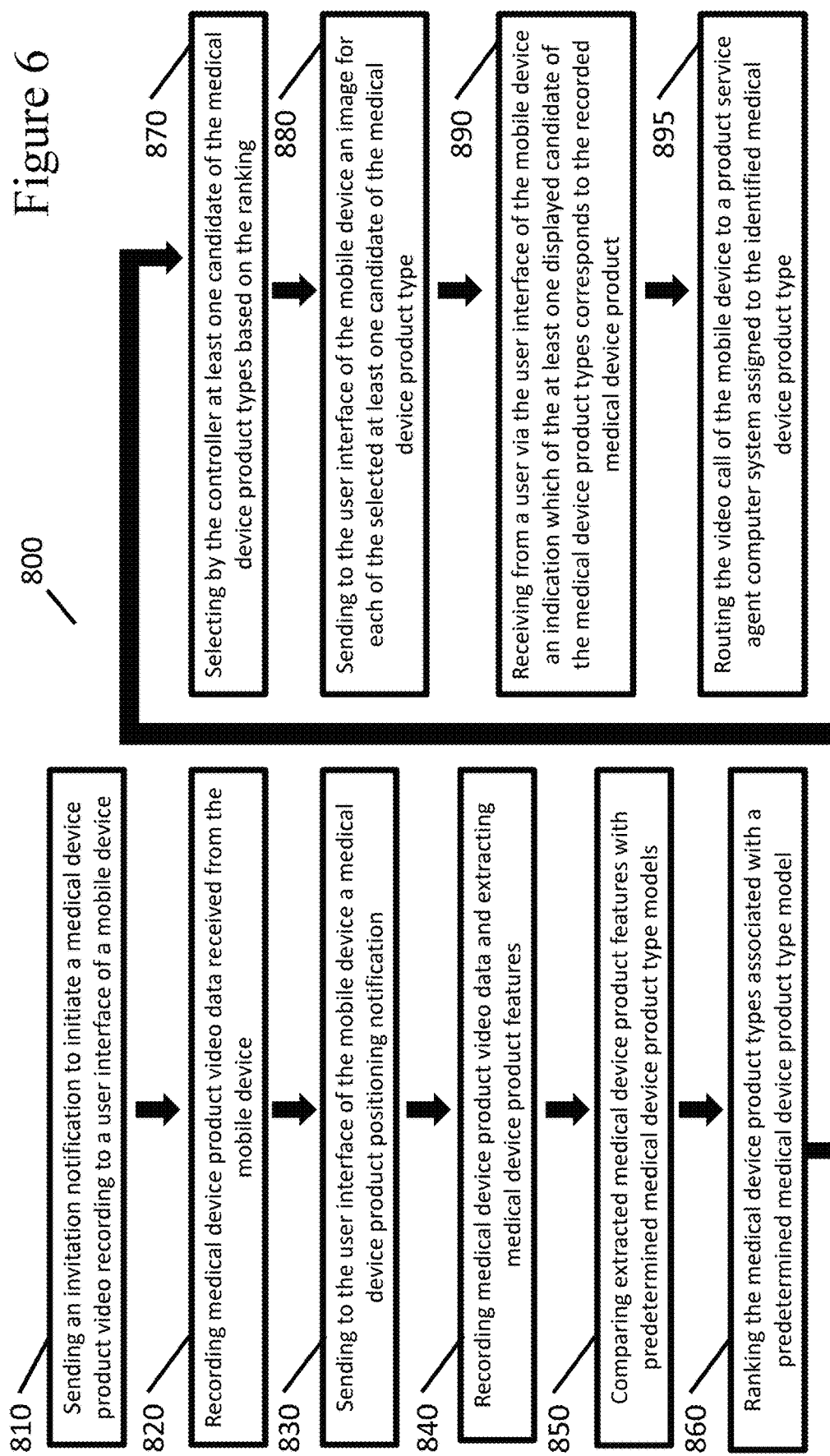
FIG. 6 depicts a flow diagram of an embodiment of this disclosure.

In the following, reference is first made to FIG. 6 which shows a workflow of the method according to an aspect of this disclosure described in more detail throughout the specification.

In the following, reference is first made to FIG. 7 which shows a workflow of the method according to an aspect of this disclosure described in more detail throughout the specification.

In the following, reference is first made to FIG. 8 which shows an example of four different medical device product types Accu-Check Aviva (1100), Accu-Check Aviva Expert (1200), Accu-Check Aviva Nano (1300) and Accu-Check Aviva Insight (1400), represented by their brand names and the corresponding markedly different product designs.

In the following, reference is first made to FIG. 9 which shows an example of four different medical device product types Accu-Check Aviva (1100), Accu-Check Aviva Expert (1200), Accu-Check Aviva Nano (1300) and Accu-Check Aviva Insight (1400), represented by their brand names and the corresponding markedly different product designs. The four different medical device product types are shown along with a medical device product type specific feature notification (270) marking up product type specific features to facilitate medical device product type identification by the user.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

| REFERENCE NUMBER LEGEND | |
|---|---|
| 100 | User |
| 110 | User's hand |
| 200 | Mobile device |
| 210 | Camera |
| 220 | Display |
| 230 | Invitation notification to initiate a medical device product video recording |
| 240 | Medical device product positioning notification (graphic and/or text) |
| 250 | Video recording status notification (graphic and/or text) |
| 260 | Notification to stop a medical device product video recording |
| 270 | Medical device product type specific feature notification |
| 300 | Medical device product |
| 300 A | Medical device product in position A |
| 300 A' | Medical device product in position A' |
| 300 B, 300 C, 300 D | Candidate medical device product types B, C and D |
| 400 | Call center computer system |
| 410 | Predetermined medical device product type model database |
| 420 | Medical device product type database |
| 430 | Medical device product type image database |
| 440 | Machine learning system |
| 450 | Controller |
| 460 | Computer user interface |
| 470 | Transceiver |
| 500 | Product service agent computer system |
| 600 | Network |
| 700 | Product service agent |
| 800 | Method for routing a video call |
| 810 | Sending an invitation notification |
| 820 | Recording medical device product video data |
| 830 | Sending a medical device product positioning notification |
| 840 | Recording medical device product video data and extracting medical device product features |
| 850 | Comparing extracted medical device product features with predetermined medical device product type models |
| 860 | Ranking the medical device product types associated with a predetermined medical device product type model |
| 870 | Selecting at least one candidate of the medical device product types based on the ranking |
| 880 | Sending an image for each of the selected at least one candidate of the medical device product type |
| 890 | Receiving an indication which of the at least one displayed candidate of the medical device product types corresponds to the recorded medical device product |
| 895 | Routing the video call of the mobile device to a product service agent computer system assigned to the identified medical device product type |

-continued

| REFERENCE NUMBER LEGEND | |
|---|---|
| 900 | Method of generating a predetermined medical device product type model |
| 910 | Receive identity of a medical device product type |
| 920 | Obtain >2 images of medical device product specimen of the medical device product type |
| 925 | Obtain >2 images of medical device product specimen of a different medical device product type |
| 930 | Obtain >2 images of medical device product specimen of the medical device product type |
| 940 | Generate predetermined model of the medical device product type using AI algorithm |
| 950 | Store predetermined model in model database |
| 1100 | Image of medical device product type Blood glucose meter "Accu-Chek Aviva" |
| 1200 | Image of medical device product type Blood glucose meter "Accu-Chek Aviva Expert" |
| 1300 | Image of medical device product type Blood glucose meter "Accu-Chek Aviva Nano" |
| 1400 | Image of medical device product type Blood glucose meter "Accu-Chek Aviva insight" |

What is claimed is:

1. A method of routing a video call from a call center computer system, to a product service agent computer system, the call center computer system having a controller, a transceiver, and a machine learning system, the method comprising:
   a) sending by the transceiver over a network to a user interface of a mobile device an invitation notification to initiate a medical device product video recording;
   b) recording medical device product video data received from the mobile device;
   c) repetitively sending by the transceiver over the network to the user interface of the mobile device a medical device product positioning notification to guide the user in positioning the medical device product into a camera of or connected to the mobile device;
   d) comparing by the machine learning system medical device product features extracted from the recorded medical device product video data to a plurality of predetermined medical device product type models, wherein each of the models is associated with a medical device product type;
   e) ranking by the machine learning system the medical device product types associated with a predetermined medical device product type model based on their degree of identity with the compared to medical device product features extracted from the recorded medical device product video data in step d);
   f) selecting by the controller at least one candidate of the medical device product types based on the ranking in step e);
   g) sending by the transceiver over the network to the user interface of the mobile device an image for each of the selected at least one candidate of the medical device product type;
   h) receiving by the controller from a user via the user interface of the mobile device an indication which of the at least one displayed candidate of the medical device product types corresponds to the recorded medical device product; and
   i) routing by the controller over the network the video call of the mobile device to a product service agent computer system assigned to the identified medical device product type.

2. The method according to claim 1, wherein steps b) and c) are repeated until the recording of the medical device product video data has been completed.

3. The method according to claim 1, further comprising sending by the transceiver over the network to the user interface of the mobile device a video recording status notification to indicate that the medical device product video recording has been completed.

4. The method according to claim 1, wherein the image for at least one identified candidate medical device product type is displayed with at least one medical device product type specific feature notification.

5. The method according to claim 1, wherein at least one further image for a candidate of the medical device product type is sent by the transceiver over the network to the user interface of the mobile device when the controller does not receive from a user via the user interface of the mobile device an indication which of the at least one displayed candidate of the medical device product types corresponds to the recorded medical device product, and wherein steps h) and i) are repeated.

6. The method according to claim 1, wherein the medical device product type is a medical device product version, generation, or release, selected from a category of a medical device product including a drug delivery device, a device for medical testing, a physiological parameter measuring device, a surgical instrument, and a wheelchair.

7. The method according to claim 1, wherein the medical device product positioning notification includes a text or a graphical element.

8. The method according to claim 1, wherein the extracted medical device product features include at least one of shape, edge, contour, size, size proportion, angle of edges, texture, color, hue, contrast of medical device product parts of different color, and pattern of the medical device product or a part thereof.

9. A call center computer system for routing a video call from the call center computer system to a medical device product service agent computer system, the call center computer system comprising:
   a transceiver configured for sending over a network to a user interface of a mobile device an invitation notification to initiate a medical device product video recording;
   a controller configured for recording medical device product video data received from the mobile device;
   the transceiver being further configured for repetitively sending over the network to the user interface of the mobile device a medical device product positioning notification to guide the user in positioning the medical device product into a camera of or connected to the mobile device;
   a machine learning system configured for
      i. comparing device product features extracted from the recorded medical device product video data to a plurality of predetermined medical device product type models wherein each of the models is associated with a medical device product type, and
      ii. ranking the medical device product types associated with a predetermined medical device product type model based on their degree of identity with the compared to medical device product features extracted from the recorded medical device product video data;
   the controller being further configured for selecting at least one candidate of the medical device product types based on the ranking;

the transceiver being further configured for sending over the network to the user interface of the mobile device an image for each of the selected at least one candidate of the medical device product type;

the controller being further adapted
   i. to receive from the user via the user interface of the mobile device an indication which of the at least one displayed candidate of the medical device product types corresponds to the recorded medical device product; and
   ii. to routing over the network the video call of the mobile device to a call-center agent computer system assigned to the identified medical device product type.

10. The call center computer system according to claim 9, further comprising:
   a medical device product type image database for storing images representing a medical device product type;
   a predetermined medical device product type model database for storing a plurality of medical device product type models each model being associated with a medical device product type.

\* \* \* \* \*